United States Patent [19]

Odenwälder et al.

[11] 4,088,491

[45] May 9, 1978

[54] LIGHT SENSITIVE PHOTOGRAPHIC MATERIAL

[75] Inventors: Heinrich Odenwälder, Cologne; Walter Püschel; Erwin Ranz, both of Leverkusen, all of Germany

[73] Assignee: Agfa-Gevaert Aktiengesellschaft, Leverkusen, Germany

[21] Appl. No.: 742,139

[22] Filed: Nov. 16, 1976

[30] Foreign Application Priority Data

Nov. 22, 1975 Germany .................. 2552505

[51] Int. Cl.$^2$ .............. G03C 7/00; G03C 5/30; G03C 1/02
[52] U.S. Cl. .............................. 96/55; 96/66.3; 96/95
[58] Field of Search ............... 96/66, 66.3, 95, 55

[56] References Cited

U.S. PATENT DOCUMENTS

| | | | |
|---|---|---|---|
| 3,043,690 | 7/1962 | Green et al. | 96/66 R |
| 4,009,029 | 2/1977 | Hammond et al. | 96/66.3 |

*Primary Examiner*—Mary F. Kelley
*Attorney, Agent, or Firm*—Connolly and Hutz

[57] ABSTRACT

High edge effects and interimage effects are provided in a color-photographic material by the use of new DIR-compounds. These are of the formula

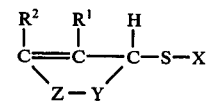

wherein
X represents together with the sulfur atom a development inhibiting group;
Y represents —O—,

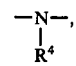

methylene group which may be alkyl substituted or a methine group;
Z represents a methylene or ethylene group which may be alkyl substituted, a methine group, a vinylene group, an o-phenylene group, a carbonyl group, an oxycarbonyl group or a carbonamide group;
$R^1$ and $R^2$ represent aliphatic, araliphatic or aromatic groups, acyl, acyloxy, alkoxy, aryloxy, amino, halogen, cyano, thioether groups or arylsulfoxyl or alkylsulfoxyl or both $R^1$ and $R^2$ together complete an at least mono-unsaturated or aromatic ring.

7 Claims, No Drawings

LIGHT SENSITIVE PHOTOGRAPHIC MATERIAL

This invention relates to a photographic material which contains compounds which react with oxidation products of color developer substances to release development inhibiting substances.

It is known to incorporate in color photographic materials compounds which release development inhibitors as a consequence of their reaction with color developer oxidation products. Compounds of this kind include, for example, the so-called DIR-couplers (DIR = Development - Inhibitor - Releasing) described in U.S. Pat. No. 3,227,554 and the so-called DIR-compounds described in U.S. Pat. No. 3,632,345.

The aforesaid DIR-couplers and DIR-compounds contain a thioether substituent in the coupling position. In the color coupling reaction this thioether substituent is split off as a diffusible mercapto compound which has development inhibiting properties and is therefore capable of influencing further development of silver halide. The use of such DIR-couplers improves the properties of the photographic materials in several respects. They can control the graininess, sharpness and gradation and thereby substantially improve the color reproduction as a whole. Reference may be had in this connection to the article entitled "Development-Inhibitor-Releasing Couplers in Photography" in "Photographic Science Engineering" 13, 74 (1969).

The known DIR-couplers inevitably release a dye together with the development inhibitor. The known DIR-compounds, on the other hand, such as those described in the above mentioned U.S. Pat. No. 3,632,345 or German Offenlegungsschriften Nos. 2,359,295; 2,362,752; 2,405,442; 2,448,063 and 2,529,350 mainly give rise to colorless compounds in their reaction with oxidized color developer.

It has been shown, however, that the known DIR-compounds are either too unstable or insufficiently reactive under certain processing conditions. If they are too unstable, the development inhibitor is not released in accordance with the image and there is therefore a general regression in sensitivity. If, on the other hand, the DIR-compounds are insufficiently reactive, the inhibitor is released too slowly and therefore has insufficient influence on the process of development.

Among the known DIR-couplers and DIR-compounds, those which are sufficiently stable in the photographic layers to release the development inhibitor imagewise are generally insufficiently reactive to influence the gradation, graininess, sharpness and interimage effects to the desired extent.

It is therefore an object of the present invention to find new compounds which, when they react with color developer oxidation products, release diffusible development inhibiting substances. These compounds must be sufficiently stable but at the same time have the necessary reactivity, in particular for producing a high edge effect, advantageously influencing the gradation curve and causing a desired interimage effect.

This problem is solved according to the invention by providing new DIR-compounds.

The invention relates to a color photographic material which contains in at least one silver halide emulsion layer or a light-insensitive binder layer associated therewith a thioether compound, preferably a non-diffusible one, which reacts with the oxidation product of a color developer substance containing a primary aromatic amino group to release a diffusible substance which inhibits development of silver halide.

The material is characterized by containing a thioether compound of the following Formula I or a tautomer thereof:

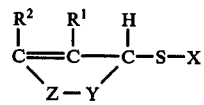

in which

X represents an aliphatic group, an aromatic group, or in particular a heterocyclic group such that, when it is split off together with the sulfur atom of the thioether bridge, it forms a diffusible mercapto compound which inhibits development of the silver halide;

Y represents —O—,

a methylene group which may be alkyl substituted or a methine group

Z represents the atoms required to complete a preferably 5- or 6-membered carbocyclic or heterocyclic ring, e.g. a methylene or ethylene group which may be alkyl substituted; a methine group

a vinylene group, an o-phenylene group, a carbonyl group, an oxycarbonyl group —O-CO— or a carbonamide group

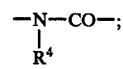

$R^1$ and $R^2$ may represent any of the substituents commonly found in the chemistry of DIR-couplers and DIR-compounds, provided they are photographically harmless. Examples include hydrogen, aliphatic, araliphatic and aromatic hydrocarbon groups which may in turn carry substituents; acyl, acyloxy such as acetoxy, alkoxy, aryloxy, e.g. phenoxy or amino, e.g. alkylarylamino, acylamino or dialkylamino including cyclic amino groups such as pyrrolidine, piperidine or morpholine; halogen, cyano or thioether groups, e.g. the group —SX; or alkylsulfoxyl or arylsulfoxyl groups;

$R^1$ and $R^2$ may also together represent the atoms required to complete an at least mono-unsaturated or aromatic, preferably 5- or 6-membered ring and they may, for example, have the following meanings:

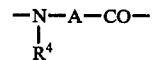  a)

  b)

c) 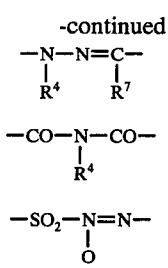

d) —CO—N—CO—
       |
       R⁴ e) —SO₂—N=N—
          |
          O

R⁴ represents hydrogen, an aliphatic group, e.g. an alkyl group with up to 22 carbon atoms, an araliphatic group, e.g. benzyl, an aromatic group, e.g. phenyl, or acyl;

R⁵ and R⁶ have each one of the meanings specified for R¹ and R² and together they may complete a condensed ring in the same way as R¹ and R², preferably a carbocyclic aromatic ring;

R⁷ represents an aliphatic group, e.g. an alkyl group with up to 22 carbon atoms or an alkoxy, arylamino, acylamino or acyl group;

A represents one or two methylene groups, a vinylene group or an o-phenylene group.

Compounds of the following Formula II and tautomers thereof are examples of particularly preferred thioether compounds for the purpose of the present invention:

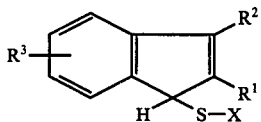

in which X, R¹ and R² have the meaning specified above and R³ represents one or more substituents selected from the group of substituents comprising having one of the substituents defined under R¹ and R² as well as nitro, halogen such as chlorine or bromine, carboxyl and sulfo.

Examples of aliphatic groups which X may represent include alkyl groups with 1 to 10 carbon atoms which may be substituted by carboxyl and/or amino groups such as CH₂-COOH and

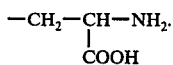

Aromatic groups represented by X may be substituted or unsubstituted phenyl or naphthyl groups such as phenyl, carboxyphenyl or nitrophenyl.

The following are examples of heterocyclic groups represented by X:
5- or 6-membered heteroaromatic groups having at least one nitrogen atom, e.g. tetrazolyl, such as 1-phenyltetrazolyl, 1-nitrophenyltetrazolyl, 1-naphthyltetrazolyl; triazolyl such as 1-phenyl-1,2,4-triazolyl; thiadiazolyl such as 2-phenylamino-1,3,4-thiadiazolyl; oxadiazolyl; thiazolyl, including benzothiazolyl and naphthothiazolyl; oxazolyl, including benzooxazolyl and naphthoxazolyl, for example 7-sulfonaphtho-[2,3-d]-oxazolyl; pyrimidyl, such as 4-methyl-6-aminopyrimidyl or 4-methyl-6-hydroxypyrimidyl; or triazinyl such as thiadiazolotriazinyl.

Compounds in which X represents a 1-phenyltetrazolyl group are particularly useful.

Acyl groups represented by the substituents R¹, R² and R³ or contained in these substituents are derived from aliphatic or aromatic carboxylic or sulfonic acids or from monoesters of carbonic acid or carbamic acid or sulfamic acids, including sulfamic acid and carbamic acids substituted with one or two substituents on the nitrogen atom, e.g. alkylcarbonyl such as acetyl or octadecanoyl; alkylsulfonyl such as hexadecylsulfonyl; aroyl such as benzoyl; arylsulfonyl such as p-tolylsulfonyl; alkoxycarbonyl such as carbethoxy; alkoxalyl such as ethoxalyl, carbamoyl such as N-ethylcarbamoyl and sulfamoyl such as hexadecylsulfamoyl.

Aliphatic groups serving as substituents represented by R¹, R² and R³ or contained in these substituents include straight or branched chain alkyl groups having up to 22 carbon atoms, e.g. methyl, ethyl, isopropyl, n-butyl, pentadecyl, or octadecyl. The alkyl groups may in turn carry substituents, e.g. hydroxyl, alkoxy, halogen, carboxyl, sulfo or aryl.

In that latter case, the alkyl groups are also described as aralkyl groups, e.g. benzyl or phenylethyl.

Aromatic groups represented by R¹, R² and R³ may be, for example, phenyl or naphthyl groups, and these may in turn be substituted.

R¹ preferably represents hydrogen, alkyl, aryl, halogen, acyloxy, amino, including substituted and cyclic amino groups, carbalkoxy, carbamoyl and alkoxy.

R² preferably represents an electron attracting group such as an acyl group, including acyl groups derived from aliphatic or aromatic carboxylic or sulfonic acids or from monoesters of carbonic acid or oxalic acid or from carbamic or sulfamic acids, thioether groups, e.g. the group —SX, alkyl or arylsulfoxyl groups and the cyano group.

It is preferred to use compounds in which at least one of the groups R¹ and R² or R³ contains a photographically inert group which confers diffusion resistance.

Groups may be regarded as conferring diffusion resistance if they make it possible for the compounds according to the invention to be incorporated in diffusion-fast form in the hydrophilic colloids which are conventionally used in photographic materials. Groups which are particularly suitable for this purpose are organic groups which may in general contain straight or branched chain aliphatic groups and may also contain isocyclic or heterocyclic aromatic groups. The aliphatic portion of these groups generally contains from 8 to 20 carbon atoms. The groups are attached to the remainder of the molecule either directly or indirectly, for example through one of the following groups: —CONH—, —SO₂NH—, —CO—, —SO₂—, —O—, —S— or —NR'— in which R' represents hydrogen or an alkyl group.

The group which confers diffusion resistance may in addition contain groups which confer solubility in water, e.g. sulfo or carboxyl groups. These may be in anionic form.

Since the diffusion properties depend on the molecular size of the whole compound used, it is sufficient in certain cases, for example if the molecule as a whole is large enough to use one or more short chain groups for conferring diffusion resistance, for example tertiary butyl, cyclopentyl or isoamyl groups.

The following are examples of thioether compounds of the general formula I:

In the following Table of formulae —SX represents the group

1)
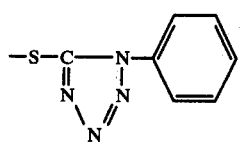
2)
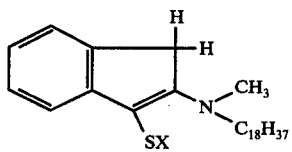
3)
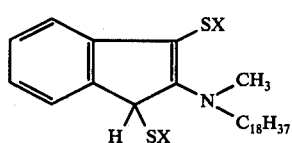
4)
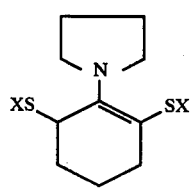
5)
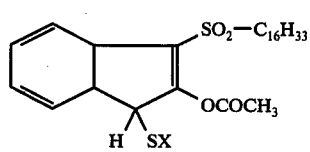
6)
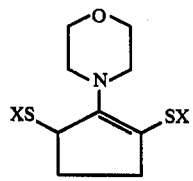
7)
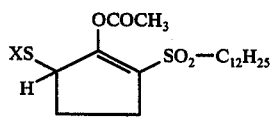
8)
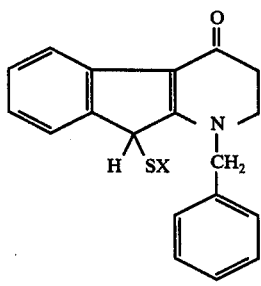
9)
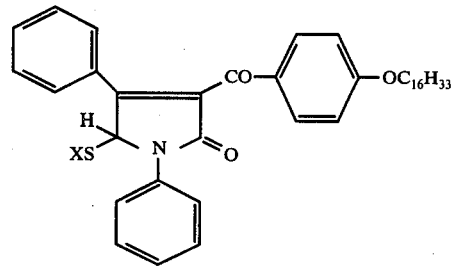
10)
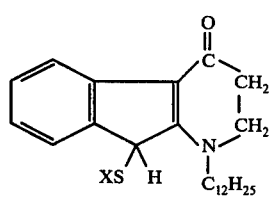
11)
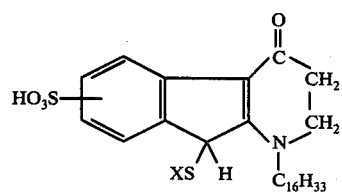
12)
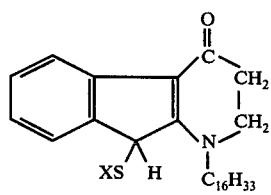
13)
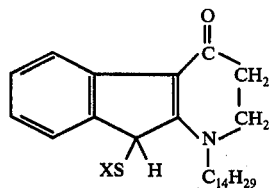
14)
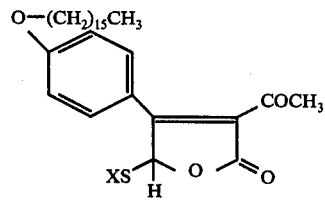
15)
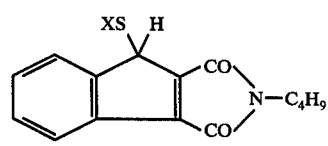
16)
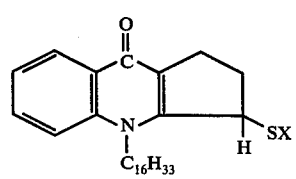

The compounds according to the present invention are generally capable of tautomerism and may therefore be present in one or other tautomeric form depending on the external conditions (solvent, pH), and may be formulated accordingly (e.g. Acta Chem. Scand. 18, 1498). Compounds of formula I may thus be represented by the following tautomeric formula Ia:

$$H-\underset{Z-Y}{\overset{R^2}{C}}-\overset{R^1}{C}=C-S-X$$

If it was said above that $R^1$ and $R^2$ together may complete a mono-unsaturated ring, then this statement was made in respect of formula I. It is understood that in a corresponding compound if its tautomeric formula Ia is considered, $R^1$ and $R^2$ may also complete a saturated ring.

The starting materials required for preparing the DIR-compounds according to the present invention can be prepared by methods described in the literature or by analogous methods. The following literature references are particularly relevant. The compounds in brackets indicate the DIR-compounds to which the particular reference is applicable:

| Liebigs Ann. Chem. 411, 350 | (Compounds 9, 23, 24) |
| J. Chem. Soc. 1954, 816 | (Compounds 14, 17) |
| J. Amer. Chem. Soc. 75, 3413 | (Compound 22) |
| J. Org. Chem. 33, 961 | (Compound 15) |
| J. Heterocyclic Chem. 11, 723 | (Compound 18) |

The indenes required as starting material for DIR compounds of formula II may generally be prepared by known methods described in Chem. Pharm. Bull. 22, 1839 (1974), Chem. Ber. 108, 138 (1975) and Chem. Ber. 33, 851.

The process carried out on these starting materials for producing the DIR compounds according to the invention is described below with reference to indenes as example but is also applicable to compounds of formula I in general.

Introduction of the mercapto group in the 1-position of the indene is carried out by reacting the indenes with the disulphide of the corresponding mercapto compound in ethanol or by introducing the inhibitor group by combining the solution of the appropriately substituted indene in an inert solvent (such as chloroform or carbon tetrachloride) with the solution of the sulphenyl chloride or sulphenyl bromide of the inhibitor in an inert solvent such as one of the solvents chloroform or carbon tetrachloride already mentioned above.

PREPARATION OF COMPOUND 4

First stage

1-Hexadecylsulphonyl-2-indanone 16.6 g of 1-bromo-2-indanone are added with stirring to a hot solution of 26.0 g of potassium hexadecylsulphinate in 100 ml of ethanol. The mixture is stirred for a further 30 minutes without further heating and then precipitated with 100 ml of water. The resulting precipitate is recrystallised from 200 ml of methanol.

The yield was 23 g and the product had a m.p. of 92° to 92.5° C.

Second stage

2-Acetoxy-3-hexadecylsulfonyl-indene 11 g of the compound obtained in Stage 1, 2.5 g of sodium acetate and 40 ml of acetic anhydride are heated together on a waterbath with stirring until dissolved. Stirring is continued for a further 30 minutes and the reaction product is then precipitated by the addition of 100 ml of methanol in an ice bath, suction filtered and washed with methanol.

The yield was 10.5 g and the product had an m.p. of 99° to 100° C.

Third stage 10 g of the compound obtained in Stage 2 and 7.5 g of 1-phenyl-tetrazole-5-disulfide in 50 ml of methyl glycol are stirred together on a waterbath for 10 minutes. Stirring is then continued for 2 hours at room temperature and the product is precipitated with methanol and water. The precipitate is suction filtered and recrystallised from 30 ml of methanol.

The yield was 11.8 g and the product had an m.p. of 74° to 75° C.

PREPARATION OF COMPOUND 12

First stage

Methyl 2-hexadecylaminopropionate 66.4 g of hexadecylamine are dissolved in 250 ml of methanol. 27 ml of methyl acrylate are added and the mixture is left to stand overnight. After removal of the solvent by distillation the residue is recrystallised from ethyl acetate.

The yield was 53 g and the product had an m.p. of 37° to 39° C.

Second stage

1-Hexadecyl-1,2,3,4-tetrahydro-9H-indeno[2,1-b]pyridine-4-one.

79.2 g of 2-indanone, 196 g of the compound obtained in Stage 1 and 15 ml of trifluoroacetic acid were heated under reflux in 800 ml of toluene for 3 hours under a nitrogen atmosphere, using a water separator. After concentration by evaporation under vacuum, the residue was dissolved hot in a mixture of 1425 ml of methanol and 75 ml of glacial acetic acid and left to cool.

The yield was 142 g and the product had a m.p. of 92° to 93.5° C.

Third stage

Compound 12

A solution of 0.2 mol of 1-phenyl-5-tetrazolyl-sulfenyl chloride in 600 ml of chloroform was added dropwise to a boiling solution of 81.8 g of the compound from Stage 2 in 1 liter of chloroform over a period of 30 minutes with stirring. Heating was then continued for a further 30 minutes under reflux. When the reaction mixture was cold, it was washed first with water, then three times with 50 ml portions of a 2N solution of sodium carbonate and finally again with water. The solution in chloroform was dried and treated in the usual manner. The residue was recrystallised twice from ethanol.

The yield was 65 g and the product had an m.p. of 73.5° to 75° C.

PREPARATION OF COMPOUND 19

5.5 g of 2-pyrrolidino-indene and 9.5 g of 1-phenyl-5-tetrazolyl-disulphide in 50 ml of ethanol were together heated under reflux for 5 minutes. The resulting precipitate was filtered hot and dissolved in chloroform, and methanol was added to the solution with cooling. Compound 4 crystallised from the solvent mixture.

The yield was 8 g and the product had an m.p. of 165° C (decomposition).

The compounds according to the invention are comparable with the known DIR couplers and DIR compounds in that they also represent non-diffusible thioether compounds which react with colour developer oxidation products to release a diffusible mercaptan which inhibits the development of silver halide. According to U.S. Pat. No. 3,148,062, DIR couplers are divided into those in which the releasable group already has an inhibitory action before coupling and those in which the inhibitory action occurs only when the group is released from the coupling position. In the latter case, the inhibitor is said to be non-preformed. According to this terminology, the compounds according to the invention are also to be described as non-diffusible compounds which react with colour developer oxidation product to release a diffusible non-preformed development inhibitor.

Compared with the known DIR couplers and DIR compounds, the compounds according to the invention are more highly reactive so that control of the gradation and the graininess and sharpness as well as edge effects and interimage effects can advantageously be improved in photographic materials by using the compounds according to the invention.

The DIR compounds according to the invention are particularly useful for obtaining high edge effects and interimage effects.

The DIR compounds according to the invention are particularly suitable for use in colour photographic multilayered materials in which the silver halide is developed by conventional colour developers after imagewise exposure, for example by the usual aromatic compounds based on p-phenylenediamine and containing at least one primary amino group.

The following are examples of suitable colour developers:
N,N-Dimethyl-p-phenylenediamine;
N,N-diethyl-p-phenylenediamine;
monomethyl-p-phenylenediamine;
2-amino-5-diethylaminotoluene;
N-butyl-N-ω-solphobutyl-p-phenylenediamine;
2-amino-5-(N-ethyl-N-β-methanesulphonamidoethylamino)-toluene;
N-ethyl-N-β-hydroxyethyl-p-phenylenediamine;
N,N-bis-(β-hydroxyethyl)-p-phenylenediamine and
2-amino-5-(N-ethyl-N-β-hydroxyethylamino)-toluene and the like.

Other suitable colour developers have been described, for example, in J.Amer.Chem.Soc. 73, 3100 (1951).

The developer compounds are normally contained in an alkaline developer bath used for treating the colour photographic material after imagewise exposure but they may also be incorporated in one or more layers of the photographic material, in which case the developer compounds may contain groups which confer diffusion resistance upon them and they may be situated in a layer which also contains a diffusion resistant colour coupler or a diffusion resistant dye-giving compound as described, for example, in U.S. Pat. No. 3,705,035.

All that is then required for development is an alkaline activator solution containing an auxiliary developer, for example phenidone. The oxidation product of the colour developer produced by development reacts with the non-diffusible colour coupler to form a non-diffusible image dye. At the same time, the oxidation product of the colour developer reacts with the non-diffusible DIR compounds according to the invention which are also present, diffusible inhibitor substances being thereby released.

The colour photographic multilayered material according to the invention contains a compound of the formula I in at least one of its layers. This DIR compound may be incorporated in a light-sensitive silver halide emulsion layer or it may be present in a hydrophilic layer of binder which is associated with a light-sensitive silver halide emulsion layer and need not itself be light-sensitive. In this context, a layer is said to be associated with a light-sensitive silver halide emulsion layer if it is spatially related to it so that significant quantities of colour developer oxidation products occur in it due to diffusion from the light sensitive silver halide emulsion layer when development takes place.

The concentration of DIR compound according to the invention in its layer may vary within wide limits, for example in the silver halide layer it may vary from $0.1 \times 10^{-3}$ to $40 \times 10^{-3}$ mol per kg of silver halide emulsion while in the associated layer of binder it may vary from 0.1 to $\times 10^{-3}$ to $10 \times 10^{-3}$ mol per gram of binder. The concentration to be used depends on the particular purpose for which the photographic material is required, the particular silver halide emulsion used and whether the DIR compound is in a silver halide emulsion layer or in a light-insensitive layer of binder. It is one advantage that the upper limit can be kept lower than the concentrations at which colour couplers are used in photographic layers since the compounds according to the invention produce excellent effects even at low concentrations.

The DIR compounds according to the invention may be used in any layer of the photographic materials, for example in one or more of the light-sensitive silver halide emulsion layers (blue-sensitive, green-sensitive or red-sensitive), or in a light-insensitive layer adjacent to one of the aforesaid light-sensitive layers. In modern colour photographic multilayer materials, the aim is to achieve high interimage effects and to improve the graininess and increase the sharpness by improvement of the edge effect in all colour forming layers. The DIR compounds are preferably used in the red-sensitive or green-sensitive silver halide emulsion layer or in an adjacent light-insensitive layer situated, for example, between the red-sensitive layer and the green-sensitive layer.

The inhibitory action of the compounds according to the invention may be produced either in the layer containing the compounds according to the invention, provided it contains developable silver halide, or in adjacent silver halide emulsion layers into which the released inhibitor is capable of diffusing. Development in each of the individual light-sensitive silver halide emulsion layers can thus be controlled in a variety of ways by means of the compounds according to the invention, and due to the vicinal effect which can be produced by the compounds according to the invention it is also possible to influence the development of one silver halide emulsion layer by the result of imagewise development in another layer so that an overall improvement in graininess, sharpness and colour reproduction can be achieved. The light-sensitive silver halide emulsion layers of the photographic material according to the invention have differing spectral sensitivities and each of them is associated with at least one non-diffusible compound for producing an image dye which is generally complementary in colour to the spectral sensitivity. These compounds may be conventional colour couplers which are generally incorporated in the silver halide layers. The red-sensitive layer, for example, contains a non-diffusible colour coupler for producing the cyan partial image, generally a coupler based on phenol or α-naphthol. The green-sensitive layer contains at least one non-diffusible colour coupler for producing the magenta partial image, generally a colour coupler based on 5-pyrazolone or indazolone. The blue sensitive layer unit contains at least one non-diffusible colour coupler for producing the yellow partial image, generally a colour coupler having an open chained keto methylene group. Colour couplers of these kinds are known in large numbers and have been described in numerous patent specifications. For example, we refer here to the publication "Farbkuppler" by W. Pelz in "Mitteilungen aus den Forschungslaboratorien der Agfa, Leverkusen/Munchen", Volume III (1961) and the publication by K. Venkataraman in "The Chemistry of Synthetic Dyes", Vol. 4, 341 to 387 Academic Press 1971.

The non-diffusible colour couplers may contain a releasable substituent in the coupling position so that they require only two equivalents of silver halide for colour formation in contrast to the usual four equivalent couplers. The colour couplers used are generally themselves colourless but if the releasable substituent contains a chromophoric group, as in the known masking couplers, the colour couplers generally have a colour which is suitable for masking unwanted side densities of the image dye by conventional masking techniques. The image dyes produced from colour couplers are generally resistant to diffusion.

If one or more silver halide emulsion layers of the material according to the invention are provided in the form of double layers consisting of two partial layers possibly having differing sensitivities or differing silver:coupler ratios, as has been variously proposed for obtaining a more advantageous sensitivity:graininess ratio, i.e. for increasing the sensitivity without coarsening the colour grain (e.g. German Pat. No. 1,121,470; U.S. Pat. No. 3,726,681 and German Offenlegungsschrift Nos. 2,322,165 and 2,416,982), one or both of these partial layers of a double layer may, according to the invention, contain one or more of the DIR compounds according to the invention.

During development, the image dyes may initially be produced in a diffusible form which is fixed only subsequently, after transfer to an image receptor layer, as is already known in various dye diffusion transfer processes, for example as disclosed in U.S. Pat. Nos. 3,227,550 and 3,628,952 and in German Patent Specification No. 1,772,929. In such cases, the light-sensitive silver halide emulsions are associated with colourless or coloured non-diffusible dye-giving compounds which release diffusible dyes in imagewise distribution when development takes place. Such dye-giving compounds are incorporated either in the silver halide emulsion layer or in an associated hydrophilic binder layer which may, for example, contain development nuclei and may also contain a silver halide which is developable without exposure.

When conventional silver halide emulsions are used in combination with non-diffusible colour couplers or non-diffusible dye-giving compounds, negative colour images are normally obtained. The DIR compounds according to the invention and also the DIR couplers, however, may advantageously also be used for reversal processes by which positive images are obtained. They are suitable both for conventional reversal processes, in which the photographic material is first subjected to black-and-white development after imagewise exposure and then colour developed after a diffuse second exposure, and for reversal processes in which the imagewise information in the photographic material is reversed due to the presence of the DIR compounds according to the invention. This reversal may take place if, for example, a colour coupler or dye-giving compound is arranged in a spontaneously developable silver halide emulsion layer, i.e. one which is developable without exposure, adjacent to a conventional silver halide emulsion layer containing a DIR compound. It is clear that for such a process it is necessary to use DIR couplers or DIR compounds which release the inhibitor very rapidly so that it will inhibit development imagewise in the spontaneously developable layer.

The non-diffusible colour couplers or dye-giving compounds as well as the non-diffusible, development-inhibitor-releasing compounds preferably used according to the invention are added to the light-sensitive silver halide emulsions or other casting solutions by the usual methods. If the compounds are soluble in water or alkalies, they may be added to the emulsions in the form of aqueous solutions, to which water-miscible organic solvents such as ethanol, acetone or dimethylformamide may be added. If the non-diffusible colour couplers, dye-giving compounds or development inhibitor releasing compounds are insoluble in water or alkalies, they may be emulsified in known manner, for example by mixing a solution of these compounds in a low boiling organic solvent with the silver halide emulsion or by first mixing it with an aqueous gelatine solution and then removing the organic solvent in the usual manner before mixing the resulting emulsion of the compound in gelatine with the silver halide emulsion. So-called coupler solvents or oil formers may be added to assist emulsification of such hydrophobic compounds. These oil formers are generally higher boiling organic compounds which enclose in the form of oily droplets the development inhibitor releasing compounds and non-diffusible colour couplers which are required to be emulsified in the silver halide emulsions. Reference to such oil formers may be found, for example, in U.S. Pat. Nos. 2,322,027; 2,533,514; 3,689,271; 3,764,336 and 3,765,897. If the compounds according to the invention are emulsified in layers with the aid of such oil formers, less stringent demand need to be made on the diffusion conferring groups in the compounds according to the invention since, in that case, shorter alkyl groups such as t-butyl or isoamyl groups are sufficient to prevent diffusion of the compounds according to the invention in the layers of photographic material. It is also possible to prepare aqueous dispersions of the DIR compounds according to the invention and add them to the casting solutions. In that case, aqueous suspensions of the compounds are finely milled, e.g. by vigorous stirring with the addition of sharp edged sand and/or by application of ultrasound, optionally in the presence of a suitable hydrophilic binder such as gelatine.

The usual silver halide emulsions may be used for the present invention. They may contain silver chloride, silver bromide or mixtures thereof, and may contain up to 20 mol % of siliver iodide. The emulsions may be either conventional negative emulsions or direct positive emulsions, for example those which have a high sensitivity in the interior of the silver halide grains, such as the emulsions described in U.S. Pat. No. 2,592,250.

The binder used for the photographic layers is preferably gelatine but this may be partly or completely replaced by other natural or synthetic binders. Suitable natural binders include e.g. alginic acid and its derivatives such as its salts, esters or amides; cellulose derivatives such as carboxymethylcellulose; alkyl celluloses such as hydroxyethylcellulose; starch or its derivatives such as ethers or esters or carrageenates. Suitable synthetic binders include polyvinyl alcohol, partially saponified polyvinyl acetate, polyvinyl pyrrolidone and the like.

The emulsions may also be chemically sensitized, for example by the addition of sulphur compounds such as allylisothiocyanate, allylthiourea, sodium thiosulphate or the like at the chemical ripening stage. Reducing agents may also be used as chemical senzitizers, for example, the tin compounds described in Belgian Patent Specifications Nos. 493,464 and 568,687, polyamines such as diethylene triamine or aminomethanesulphinic acid derivatives, e.g. according to Belgian Patent Specification No. 547,323.

Noble metals such as gold, platinum, palladium, iridium, ruthenium or rhodium and compounds of these metals may also be used as chemical sensitizers. This method of chemical sensitization has been described in the article by R. Koslowsky, Z.Wiss.Phot. 46, 65 - 72 (1951).

The emulsions may also be sensitized with polyalkylene oxide derivatives, e.g. with a polyethylene oxide having a molecular weight of between 1000 and 20,000, or with condensation products of alkylene oxides and aliphatic alcohols, glycols or cyclic dehydration products of hexitols, or with alkyl substituted phenols, aliphatic carboxylic acids, aliphatic amines, aliphatic diamines or amides. The condensation products should have a molecular weight of at least 700 and preferably more than 1000. One may, of course, also use combinations of these sensitizers for obtaining special effects, as described in Belgian Patent Specification No. 537,278 and British patent specification No. 727,982.

The emulsions may also be spectrally sensitized, e.g. by the usual monomethine or polymethine dyes such as acid or basic cyanines, hemicyanines, streptocyanines, merocyanines, oxonoles, hemioxonoles, styryl dyes, etc. or trinuclear or higher nuclear methine dyes, for example, rhodacyanines or neocyanines. Sensitizers of this kind have been described, for example, in the work by F. M. Hamer "The Cyanine Dyes and Related Compound" (1964), Interscience Publishers John Wiley and Sons.

The emulsions may contain the usual stabilizers such as homopolar or salt-like compounds of mercury containing aromatic or heterocyclic rings, such as mercapto triazoles, or simple mercury salts, sulphonium mercury double salts and other mercury compounds. Azaindenes are also suitable stabilizers, preferably tetra- or pentaazaindenes and especially those which are substituted with hydroxyl or amino groups. Compounds of this kind have been described in the article by Birr, Z.Wiss. Phot. 47, 2 - 27 (1952). Other suitable stabilizers include heterocyclic mercapto compounds, e.g. phenylmercapto-tetrazole, quaternary benzothiazole derivatives, benzotriazole and the like.

The emulsions may be hardened in the usual manner, for example with formaldehyde or halogen substituted aldehydes containing a carboxyl group, such as mucobromic acid, diketones, methanesulphonic acid esters, dialdehydes and the like.

The photographic layes may also be hardened with epoxide hardeners or heterocyclic ethylene imine or acryloyl hardeners. Examples of suitable hardeners have been described, for example, in German Offenlegungsschrift No. 2,263,602 and British patent specification No. 1,266,655. The layers may also be hardened by the process according to German Offenlegungsschrift No. 2,218,009 to produce colour photographic materials suitable for high temperature processing.

The photographic layers or colour photographic multilayered material may also be hardened with hardeners based on diazine, triazine or 1,2-dihydroquinoline as described in British patent specifications No. 1,193,290; 1,251,091; 1,306,544 or 1,266,655; French patent specification No. 7,102,716 or German Offenlegungsschrift No. 2,332,317. Examples of such hardeners include diazine derivatives containing alkyl-sulphonyl or arylsulphonyl groups, derivatives of hydrogenated diazines or triazines such as 1,3,5-hexahydrotriazine, fluorosubstituted diazine derivatives such as fluoropyrimidines and esters of 2-substituted 1,2-dihydroquinoline- or 1,2-dihydroisoquinoline-N-carboxylic acids. Vinyl sulphonic acid hardeners and carbodiimide or carbamoyl hardeners are also suitable, e.g. those described in German Offenlegungsschriften No. 2,263,602; 2,225,230 and 1,808,685; French Patent Specification No. 1,491,807; German Patent Specification No. 872,153 and DDR Patent Specification No. 7,218. Other suitable hardeners have been described, for example, in British patent specification No. 1,268,550.

The materials according to the invention may be, for example, positive, negative or reversal materials on the usual support layers used for photographic materials, for example foils of cellulose nitrate, cellulose acetate such as cellulose triacetate, polystyrene, polyesters such as polyethylene terephthalate, polyolefines such as polyethylene or polypropylene, baryta paper substrates or polyolefine-backed paper substrates, e.g. polyethylene backed paper, as well as glass or the like.

EXAMPLES

The DIR compounds are preferably used in multilayered combinations such as those conventionally used for the preparation of light-sensitive negative or positive photographic colour materials.

The effect of the DIR compounds according to the invention is demonstrated below with the aid of the example of a typical combination of layers or partial layers used for colour negative materials.

Light sensitive photographic material:

Arrangement of the layers (a) Support: Substrated cellulose triacetate support.
(a) Intermediate gelatine layer (1 μ)
(b) Cyan layer consisting of an emulsion sensitized to the red spectral region and a colour coupler for cyan (silver application: 4 g of Ag/m²);
(c) Intermediate gelatine layer (1μ)
(d) Magenta layer consisting of an emulsion sensitized to the green spectral region and a colour coupler for magenta (silver application: 3.5 g of Ag/m²)
(e) Intermediate gelatine layer (1μ)
(f) Yellow filter layer (2 μ)
(g) Yellow layer consisting of an emulsion which is sensitive to the blue spectral region and a colour coupler for yellow (silver application 1.5 g of Ag/m²)
(h) Protective gelatine layer (1μ)

The material is hardened in the usual manner, e.g. with tris-acryloylhexahydrotriazine. The individual red-sensitive (b), green-sensitive (d) and blue-sensitive (g) partial layers are prepared by casting the following solutions:

(b) 1 kg of a red-sensitized halide emulsion (100 g of Ag/kg emulsion) in which the silver halide consists of 95 mol % of silver bromide and 5 mol % of silver iodide, 50 ml of a 1% solution of 1,3,3a,7-tetraza-4-hydroxyl-6-methylindene in methanol, 360 g of a coupler dispersion of a solution of 15 g of cyan coupler of the following formula

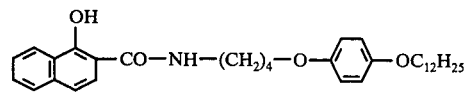

in 7.5 g of dibutylphthalate,
30 g of diethylcarbonate,
100 ml of a 4% aqueous gelatine solution,
0.8 g of Mersolat (wetting agent, sulphonated paraffin-hydrocarbons)
10 ml of a 10% aqueous saponin solution and 1000 ml of water.

(d) The composition of the casting solution for the green sensitive layer is similar to that for the red sensitive layer (b) except that the emulsion is sensitized to the green region of the spectrum and, instead of cyan coupler dispersion, it contains 192 g of a dispersion of magenta coupler of the following formula

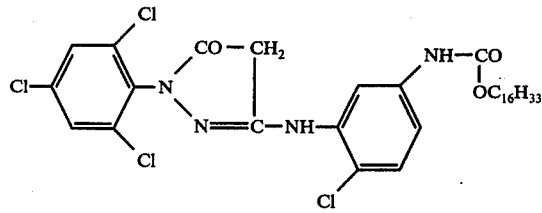

in a similar composition to the cyan emulsion in layer (b).

(g) The composition of casting solution for the blue sensitive layer is similar to that used for the red sensitive layer (b) except that the emulsion is sensitive only to the blue region of the spectrum and, instead of cyan coupler dispersion, it contains 175 g of a 5% solution of yellow coupler of the following formula

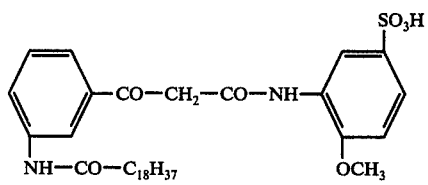

in an aqueous 8% gelatine solution.

The gelatine layers (a), (c), (e) and (h) are prepared by casting the following solution:
125 ml of a 10% gelatine solution,
500 ml of water,
5 ml of a 10% aqueous solution of saponin.

The casting solution for the yellow filter layer is the same as the casting solution for gelatine layers (a), (c), (e) and (h) except for the addition of
1.4 g of finely dispersed metallic silver of the kind generally used as barrier filter for the blue spectral portion of light.

PROCESSING

The material is exposed behind a grey step wedge and colour separation filters blue, green and red in a conventional sensitometer and then developed in a colour developer of the following composition:
2 g of sodium salt of isopropanoldiaminotetracetic acid,
30 g of potassium carbonate
4 g of potassium sulphite
1.5 g of potassium bromide
2 g of hydroxylamine
5 g of the colour developer of the following formula

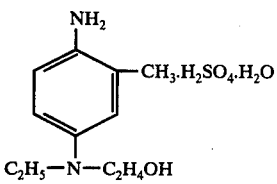

made up to 1 liter. pH adjusted to 10.2. Development: 3¼ minutes at 38° C.

The subsequent processing stages indicated below are each carried out for 3¼ minutes. The bath temperatures are again 38° C in each case.
Short stop bath:
30 ml of acetic acid (concentrated)
20 g of sodium acetate
water up to liter
Rinsing
Bleaching bath:
100 g of potassium ferricyanide
15 g of potassium bromide
water up to 1 liter
Rinsing
Fixing bath: 20% aqueous solution of sodium thiosulphate
Final Rinsing.

Assessment of the exposed and developed samples:

Since the experimental material is not masked, the side densities of the resulting dyes interfere with determination of the true IIE. To eliminate the error due to side densities, gradation curves are drawn up from the analytical densities calculated by converting the measured integral densities. These analytic colour density curves are used for obtaining the $\gamma$ values on which the IIE measurement is based. The IIE is defined as follows:

$$IIE = \frac{\gamma s - \gamma w}{0.6} \cdot 100\%$$

s: Selective exposure
w: White exposure

The graininess is given in $\gamma_D$-values (rms-values for shutter diameter of 29 $\mu$) by the method described by H. T. BUSCHMANN in "Bestimmung der Kornigkeit photographischer Schichten mit Hilfe digitaler Technik" in Optik 38, 1973, pages 169 – 219.

EXAMPLE 1

Incorporation of DIR-compound 20 in red sensitive layer (b).

DIR-compound 20 is dispersed as follows:

A solution of 4.9 g of Compound No. 20 in 3 g of tricresyl phosphate and 12 ml of ethyl acetate is emulsified in a solution of 100 ml of a 4% aqueous gelatine solution and 0.8 g of Mersolat (wetting agent; sulfonated paraffin hydrocarbons) by vigorous stirring in a mixing siren. Arrangement of layers: layers (a), (b) and (c).

Sample 1

No DIR-compound in layer (b).

Sample 2

Layer (b) contains DIR-compound 20. 42 g of emulsion of DIR-compound 20 are added to 1 kg of emulsion for the casting solution of the layer.

The samples were exposed to red light behind a step wedge and developed as indicated above. The inhibitory action of the DIR-compound causes a reduction of gradation from $\gamma = 1.50$ (sample 1) to $\gamma = 0.70$ (sample 2). If the quantity of silver halide and color coupler used for preparing the comparison sample without DIR-compound is reduced (sample 1a) so that a gradation of 0.70 is also obtained, it is found that the graininess of sample 2 containing the DIR-compound is substantially less than that of sample 2a although sample 2 has the same gradation and at least equal sensitivity:

|  | Sample 1a | Sample 2 |
|---|---|---|
| Graininess $\delta D \cdot 10^{-2}$ at density D = 1 | 2.3 | 1.2 |

EXAMPLE 2

Incorporation of DIR-compound 4 in intermediate gelatine layer (c).

DIR-compound 4 is emulsified in a comparable molar quantity to that indicated in Example 1.

A complete arrangement of layers — layers (a) to (h) — is prepared in which the DIR-compound is incorporated in the intermediate gelatine layer (c), in other words, between the red sensitive and the green sensitive layer (Sample 1). The casting solution for the modified gelatine layer (c) has the following composition:

50 ml of a 10% gelatine solution
33 g of emulsion of DIR-compound 4
500 g of water
7 ml of a 10% aqueous solution of saponin.

Layer (c) is applied in a thickness of 1.5 μ.

A complete arrangement of layers containing an ordinary intermediate gelatine layer (c) is prepared for comparison (Sample 2).

The samples were exposed to red, green and white light behing a step wedge and processed as described above.

The results show that the presence of the DIR-compound during red exposure, i.e. for development of the cyan layer (b) completely prevents any accompanying development of magenta layer (d) such as occurred to a certain extent in sample 2.

Similarly, the presence of the DIR-compound in the intermediate layer (c) during green exposure, i.e. for development of the magenta layer (d), completely prevents concomitant development of the cyan layer (b). The DIR-compound absorbs the developer oxidation product diffusing form the adjacent layers by entering into a coupling reaction with it. This releases the inhibitor which diffuses into the adjacent red sensitive and green sensitive layers where it inhibits development. The resulting interimage effect (IIE) is represented in the following table:

| Sample | IIE% Cyan | IIE% Magenta | Red exposure Cyan$_{\gamma_s}$ | Green exposure Magenta$_{65_s}$ | Cyan | White exposure Magenta$_{\gamma_w}$ |
|---|---|---|---|---|---|---|
| 1 | 82 | 52 | 1.02 | 0.86 | 0.53 | 0.55 |
| 2 | 30 | 20 | 1.35 | 1.29 | 1.17 | 1.17 |

The table clearly shows that the DIR-compound incorporated in the intermediate gelatine layer (c) considerably increases the IIE both in the cyan layer and in the magenta layer.

EXAMPLE 3

Incorporation of DIR-compound in the magenta layer (d) of a complete arrangement of layers — layers (a) to (h) -:

DIR-compound 12 and, for comparison, Compound No. 1 of German Offenlegungsschrift No. 2 405 442 (A) and Compound No. 7 of German Offenlegungsschrift No. 2 359 295 (B) are emulsified in comparable molar quantities as described in Example 1. Comparable molar quantities of emulsions or solutions of DIR-compound are added to the casting solution for layer (d), (e.g. in the case of Sample 1, DIR-compound No. 12, 50 g of dispersion to 1 kg of silver halide emulsion). Sample 4 contains no DIR-compound in layer (d).

The samples were exposed to red, green and white light behind a step wedge and developed as described above.

The activity of the DIR-compounds can be seen from the magenta-$\gamma$-values of the green exposure (magenta-$\gamma_s$). The influence of the DIR-compound present in the magenta layer on the IIE of the cyan layer was also examined.

| Sample | DIR-Compound | IIE% Cyan | Red Cyan$_{\gamma_s}$ | Green Magenta$_{\gamma_s}$ | White Cyan$_{\gamma_w}$ |
|---|---|---|---|---|---|
| 1 | 12 | 131 % | 1.43 | 0.40 | 0.64 |
| 2 | A | 35 % | 1.42 | 1.09 | 1.21 |
| 3 | B | 48 % | 1.39 | 1.06 | 1.10 |
| 4 | — | 27 % | 1.40 | 1.32 | 1.24 |

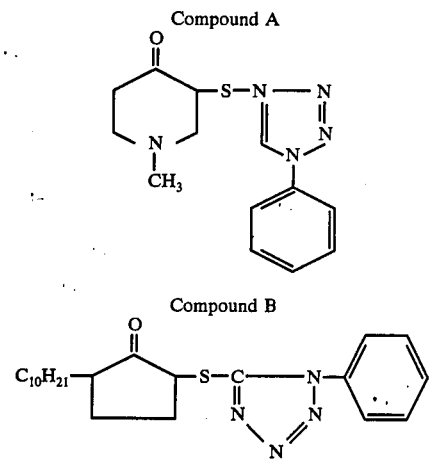

Compound A

Compound B

The table clearly shows (magenta $\gamma_s$) that DIR-compound 12 (Sample 1) has the most powerful inhibitory effect, i.e. is most active, in the magenta layer in which it is incorporated. The other DIR-compounds are less active. After exposure to white light the inhibitor released from DIR-compound 12 in the magenta layer by development and diffused into the cyan layer also vigorously inhibits development of the cyan layer so that a powerful cyan IIE (131%) is produced. The DIR-compounds A and B cause substantially less increase in the IIE in the adjacent 1a cyan layer which exists even without DIR-coupler (sample 4).

Similar results are obtained when other compounds according to the invention are used instead of compound 12.

EXAMPLE 4

Incorporation of DIR-compounds 4, 7 and 20, using in each case the same DIR-compound in the magenta layer as in the cyan layer of the whole arrangement of 5 layers (a) to (h). The magenta partial color layer (d) is arranged in two partial layers above one another according to the double layer principle.

The lower partial layer d1 contains a green sensitized silver halide emulsion in which the silver halide consists of 93 mol-% of silver bromide and 7 mol-% of silver iodide. This layer contains 35 g of the given magenta coupler to 1 kg of emulsion.

The upper partial layer d2 contains a more highly sensitive, coarser-grained green-sensitized silver halide emulsion in which the silver halide consists of 95 mol-% of silver bromide and 5 mol-% of silver iodide. The proportion of magenta coupler in this layer is 10 g to 1 kg of emulsion.

Layer d1 is less sensitive than layer d2 by about 0.5 log I.t units.

DIR-compounds 4, 7 and 20 are emulsified in comparable molar quantities as described in Example 1 and added to layers d1 (22 g of dispersion to 1 kg of silver halide) and b (20 g of dispersion to 1 kg of silver halide).

The sensitivity of the magenta double layer is about 0.2 log I.t units higher (measured according to the criterion of 0.2 density units above fog) than that of the individual magenta layer in the layer combination of Example 3 for a comparable graininess.

| Sample | DIR-Compound in magenta (d1) and cyan (b) layer | IIE % Cyan | Magenta | Exposure | | | |
|---|---|---|---|---|---|---|---|
| | | | | Red Cyan$_s$ | Green Magenta$_s$ | White Cyan$_w$ | Magenta$_2$ |
| 1 | 4 | 67 | 58 | 0.95 | 1.05 | 0.55 | 0.70 |
| 2 | 7 | 70 | 60 | 0.91 | 1.01 | 0.49 | 0.65 |
| 3 | 20 | 58 | 45 | 1.05 | 1.14 | 0.70 | 0.87 |
| 4 | no DIR-compound | 17 | 8 | 1.45 | 1.49 | 1.35 | 1.44 |

The table shows that both a high magenta IIE and a high cyan IIE are obtained when the same DIR-compound is used in the red sensitive and the green sensitive partial color layer.

We claim:

1. A color photographic process for producing color images, which comprises imagewise exposing a light sensitive color photographic multi-layer material having at least one silver halide emulsion layer on a support and associated with that layer a non-diffusible DIR compound capable of reacting with the oxidation product of the color developer to release in imagewise distribution a diffusible mercapto compound which inhibits development of silver halide.

and color developing the imagewise exposed photographic material in the presence of the thioether DIR compound, and in the presence of a color coupler to form an image dye wherein the improvement comprises the color development is carried out in the presence of a thioether compound of the following Formula I or a tautomer thereof

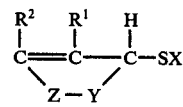

in which
X represents an aliphatic, aromatic or heterocyclic group such that when it is split off together with the sulfur atom of the thioether bridge it forms a diffusible mercapto compound which inhibits development of silver halide;
Y represents —O—,

a methylene group which may be alkyl substituted or a methine group

Z represents a methylene or ethylene group which may be alkyl substituted, a methine group

a vinylene group, an o-phenylene group, a carbonyl group, an oxycarbonyl group —O—CO— or a carbonamide group

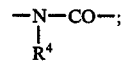

$R^1$ and $R^2$ which may be the same or different represent hydrogen, aliphatic, araliphatic or aromatic hydrocarbon groups, acyl, acyloxy, alkoxy, aryloxy, amino, halogen, cyano, thioether groups or alkylsulfoxyl or arylsulfoxyl, $R^1$ and $R^2$ together represent the group required to complete a ring having at least one double bond or aromatic ring,
$R^4$ represents hydrogen, alkyl having up to 22 carbon atoms, aralkyl, aryl or acyl,
$R^5$ and $R^6$ have each one of the meanings indicated for $R^1$ and $R^2$ or together represent the group required to complete a ring having at least one double bond or aromatic ring.

2. The color photographic development process as claimed in claim 1 in which the color development is carried out in the presence of a thioether compound of the following Formula II

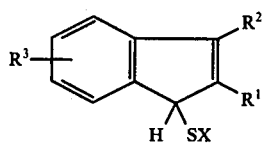

in which X, $R^1$ and $R^2$ have the meaning indicated in claim 1 and $R^3$ represents one or more of the same or different substituents selected from the group of substituents comprising substituents defined under $R^1$ and $R^2$ as well as nitro, halogen, carboxyl and sulfo.

3. A light sensitive color photographic material comprising at least one light-sensitive silver halide emulsion layer and containing distributed therein or in a binder layer associated therewith a thioether compound resistant to diffusion capable of reacting with the color developer oxidation product to release a diffusible mercapto compound which inhibits development of silver halide, wherein the improvement comprises the DIR-compound contained in the material is a thioether compound of the following Formula I or a tautomer thereof

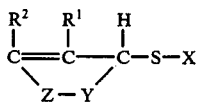

in which
X represents an aliphatic, aromatic or heterocyclic group such that when it is split off together with the sulfur atom of the thioether bridge it forms a diffusible mercapto compound which inhibits the development of silver halide;
Y represents —O—,

a methylene group which may be substituted or a methine group

Z represents a methylene or ethylene group which may be alkyl substituted, a methine group

an o-phenylene group, a carbonyl group, an oxycarbonyl group —O—CO— or a carbonamide group

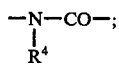

$R^1$ and $R^2$ are the same or different and represent hydrogen, aliphatic, araliphatic or aromatic hydrocarbon groups, acyl, acyloxy, alkoxy, aryloxy, amino, halogen, cyano, thioether groups, alkyl, sulfoxyl or aryl sulfoxyl; $R^1$ and $R^2$ together represent the atoms required to complete a ring having at least one double bond or aromatic ring;
$R^4$ represents hydrogen, an alkyl group having up to 22 carbon atoms or an aralkyl, aryl or acyl group;
$R^5$ and $R^6$ each have one of the meanings specified for $R^1$ and $R^2$ or together complete an at least monounsaturated or aromatic, carbocyclic or six-membered heterocyclic ring; at least one of the groups $R^1$ and $R^2$ or a ring completed by $R^1$ and $R^2$ or by Z and Y carries a group which confers diffusion resistance.

4. The color photographic material as claimed in claim 3 in which the DIR-compound contained in it is a thioether compound of the following Formula II

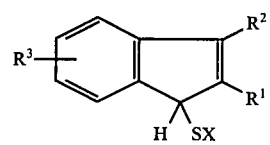

in which X, $R^1$ and $R^2$ have the meanings specified in claim 1 and $R^3$ represents one or more of the same or different substituents selected from the group comprising substituents defined under $R^1$ and $R^2$ as well as nitro, halogen, carboxyl or sulfo, and in which at least one of the groups $R^1$, $R^2$ and $R^3$ carries a group which confers diffusion resistance.

5. Color photographic material as claimed in claim 4 in which $R^2$ is an acyl group, a thioether group, an alkylsulfoxyl or an arylsulfoxyl group or a cyano group.

6. Color photographic material as claimed in claim 4 in which $R^1$ represents hydrogen, alkyl, alkoxy, aryl, halogen, amino, acyloxy, carbalkoxy or carbamoyl.

7. Color photographic material as claimed in claim 4 in which $R^1$ and $R^2$ together represent one of the following:

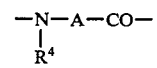 a)

 b)

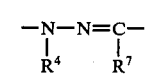 c)

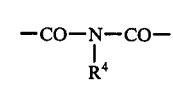 d)

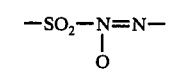 e)

in which
A represents a methylene group, an ethylene group, a vinylene group or an o-phenylene group;
$R^4$ represents hydrogen, an alkyl group having up to 22 carbon atoms or an aralkyl or aryl group; and
$R^7$ represents an alkyl group having up to 22 carbon atoms or an alkoxy, arylamino, acylamino or acyl group.

* * * * *